United States Patent
Mohr

(10) Patent No.: US 9,216,061 B2
(45) Date of Patent: Dec. 22, 2015

(54) MEDICAL DEVICE WITH ORIENTABLE TIP FOR ROBOTICALLY DIRECTED LASER CUTTING AND BIOMATERIAL APPLICATION

(71) Applicant: Intuitive Surgical Operations, Inc., Sunnyvale, CA (US)

(72) Inventor: Catherine J. Mohr, Mountain View, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 14/625,036

(22) Filed: Feb. 18, 2015

(65) Prior Publication Data

US 2015/0157407 A1    Jun. 11, 2015

Related U.S. Application Data

(62) Division of application No. 11/964,936, filed on Dec. 27, 2007, now Pat. No. 9,043,018.

(51) Int. Cl.
| | |
|---|---|
| A61B 1/00 | (2006.01) |
| A61B 18/24 | (2006.01) |
| A61B 19/00 | (2006.01) |
| A61B 17/00 | (2006.01) |
| A61B 18/00 | (2006.01) |

(52) U.S. Cl.
CPC ............. *A61B 18/24* (2013.01); *A61B 19/2203* (2013.01); *A61B 17/00491* (2013.01); *A61B 19/56* (2013.01); *A61B 2017/00203* (2013.01); *A61B 2017/00314* (2013.01); *A61B 2018/00601* (2013.01); *A61B 2019/2211* (2013.01); *A61B 2019/2223* (2013.01); *A61B 2019/2234* (2013.01); *A61B 2019/2238* (2013.01); *A61B 2019/2242* (2013.01); *A61B 2019/2273* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,337,732 | A * | 8/1994 | Grundfest et al. | 600/116 |
| 5,662,587 | A * | 9/1997 | Grundfest et al. | 600/114 |
| 5,823,993 | A * | 10/1998 | Lemelson | 604/503 |
| 5,919,135 | A * | 7/1999 | Lemelson | 600/407 |
| 6,309,397 | B1 * | 10/2001 | Julian et al. | 606/130 |
| 6,493,608 | B1 * | 12/2002 | Niemeyer | 700/302 |

(Continued)

OTHER PUBLICATIONS

Kitchens, Susan, "Reflection Perfection," Forbes.com, 2 pages, Jun. 5, 2006, Internet: <http://www.forbes.com/business/forbes/2006/0605/078.html>.

(Continued)

*Primary Examiner* — Jonathan L Sample

(57) ABSTRACT

A medical device used in a medical robotic system has a conduit and an orientable tip. An optical fiber coupled to a laser source and/or a catheter coupled to one or more biomaterial sources extends through the conduit and tip so that the tip of the medical device may be robotically directed towards a target tissue for laser and/or biomaterial application as part of a medical procedure performed at a surgical site within a patient. A protective sheath covers the fiber as it extends through the conduit and tip. A first coupler adjustably secures at least the sheath to the medical device and a second coupler adjustably secures the fiber to at least the sheath. A similar dual coupler mechanism may be used to secure the sheathed catheter to the medical device.

10 Claims, 9 Drawing Sheets

(56) References Cited

U.S. PATENT DOCUMENTS

| | | | |
|---|---|---|---|
| 6,645,196 B1* | 11/2003 | Nixon et al. | 606/1 |
| 6,817,974 B2* | 11/2004 | Cooper et al. | 600/142 |
| 6,986,739 B2* | 1/2006 | Warren et al. | 600/159 |
| 7,001,431 B2* | 2/2006 | Bao et al. | 623/17.12 |
| 7,083,615 B2* | 8/2006 | Peterson et al. | 606/41 |
| 7,090,683 B2* | 8/2006 | Brock et al. | 606/130 |
| 7,125,403 B2* | 10/2006 | Julian et al. | 606/1 |
| 7,727,230 B2* | 6/2010 | Fuimaono et al. | 606/41 |
| 2002/0082610 A1* | 6/2002 | Cioanta et al. | 606/108 |
| 2002/0087151 A1* | 7/2002 | Mody et al. | 606/15 |
| 2002/0128636 A1* | 9/2002 | Chin et al. | 606/16 |
| 2002/0193735 A1* | 12/2002 | Stiger | 604/101.01 |
| 2003/0163128 A1* | 8/2003 | Patil et al. | 606/41 |
| 2003/0220649 A1* | 11/2003 | Bao et al. | 606/90 |
| 2004/0024385 A1* | 2/2004 | Stuart | 606/1 |
| 2004/0049205 A1* | 3/2004 | Lee et al. | 606/130 |
| 2004/0111183 A1* | 6/2004 | Sutherland et al. | 700/245 |
| 2004/0254566 A1* | 12/2004 | Plicchi et al. | 606/1 |
| 2005/0182418 A1* | 8/2005 | Boyd et al. | 606/92 |
| 2005/0203382 A1* | 9/2005 | Govari et al. | 600/424 |
| 2005/0251156 A1* | 11/2005 | Toth et al. | 606/153 |
| 2006/0122674 A1* | 6/2006 | Eshel | 607/105 |
| 2006/0178556 A1* | 8/2006 | Hasser et al. | 600/102 |
| 2006/0199999 A1* | 9/2006 | Ikeda et al. | 600/141 |
| 2006/0201130 A1* | 9/2006 | Danitz | 59/78.1 |
| 2007/0005002 A1* | 1/2007 | Millman et al. | 604/30 |
| 2007/0013336 A1* | 1/2007 | Nowlin et al. | 318/568.21 |
| 2007/0016174 A1* | 1/2007 | Millman et al. | 606/1 |
| 2007/0032701 A1* | 2/2007 | Fowler et al. | 600/173 |
| 2007/0038300 A1* | 2/2007 | Bao et al. | 623/17.12 |
| 2007/0100199 A1* | 5/2007 | Lau et al. | 600/37 |
| 2007/0142970 A1* | 6/2007 | Burbank et al. | 700/251 |
| 2007/0142971 A1* | 6/2007 | Schena | 700/251 |
| 2007/0156017 A1* | 7/2007 | Lamprecht et al. | 600/102 |
| 2007/0156121 A1* | 7/2007 | Millman et al. | 606/1 |
| 2007/0225634 A1* | 9/2007 | Ferren et al. | 604/27 |
| 2007/0239172 A1* | 10/2007 | Lee et al. | 606/130 |
| 2008/0046122 A1* | 2/2008 | Manzo et al. | 700/245 |
| 2008/0103564 A1* | 5/2008 | Burkinshaw et al. | 607/96 |
| 2008/0167610 A1* | 7/2008 | Dann et al. | 604/104 |
| 2008/0221550 A1* | 9/2008 | Lee | 604/508 |
| 2009/0082609 A1* | 3/2009 | Condado | 600/4 |
| 2009/0088775 A1* | 4/2009 | Swarup et al. | 606/130 |
| 2009/0099520 A1* | 4/2009 | Millman et al. | 604/131 |
| 2009/0171372 A1 | 7/2009 | Mohr | |
| 2010/0063630 A1* | 3/2010 | Sutherland et al. | 700/264 |

OTHER PUBLICATIONS

McLeod, Ian K. et al. "Potential applications of the da Vinci minimally invasive surgical robotic system in otolaryngology," ENT-Ear, Nose & Throat Journal, vol. 84, No. 8; Aug. 2005, pp. 483-487.

Micromedics, Fibrijet II.I Ratio Applicator assembly instructions, 1 page, no date, Internet: <http://www.micromedics-usa.com/products/biomaterials/FibriJet_Easy_Assembly.pdf>.

Omniguide, "Endoscopic Skull Base Surgery," 1 page, No date, Internet: <http://www.omni-guide.com/Pages/Applic_SBT.html>.

Omniguide, "Laryngeal Surgery," 1 page, no date, Internet: <http://www.omni-guide.com/Pages/Applic_LS.html>.

Omniguide, "Papilloma," 1 page, no date, Internet: <http://www.omni-guide.com/Pages/Applic_Papilloma.html>.

Omniguide, "Product Overview," 2 pages, no date, Internet: <http://www.omni-guide.com/Pages/Tech_ProductsOverview.html>.

Omniguide, "Tracheal Stenosis," 1 page, No date, Internet: <http://www.omni-guide.com/Pages/Applic_TS.html>.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

MEDICAL DEVICE WITH ORIENTABLE TIP FOR ROBOTICALLY DIRECTED LASER CUTTING AND BIOMATERIAL APPLICATION

CROSS REFERENCE TO RELATED APPLICATIONS

This application is a divisional of application Ser. No. 11/964,936 filed Dec. 27, 2007, which is incorporated herein by reference.

FIELD OF THE INVENTION

The present invention generally relates to medical devices used in medical robotic systems and in particular, to a medical device with an orientable tip for robotically directed laser cutting and biomaterial application during a medical procedure performed by a surgeon using a medical robotic system.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

In another example of a medical robotic system, a robotically manipulated endoluminal device may be employed that enters the patient through a single minimally invasive incision or through a body orifice, such as the mouth, rectum, vagina, or urethra, to reach a surgical or diagnostic site within a patient by passing, at least partially along with way, through a natural body lumen. The endoluminal device in this case may integrate surgical instruments and an image capturing device into one unit.

One application for such an endoluminal device is Natural-Orifice Transluminal Endosurgery ("NOTES"), which may involve, for example, passing flexible instruments through one of the body's orifices and entering the abdomen from the inside of the patient, rather than through a minimally invasive incision from the outside. For example, in "transgastric" surgery, instruments are passed through the mouth and into the stomach. A hole is then cut in the stomach wall to perform a medical procedure within the abdominal cavity. Once the procedure is completed, the instruments are withdrawn along with any tissue removed during the procedure, and the entry hole is stitched back up. Because the stomach wall has very few pain receptors, NOTES may be less painful than even minimally invasive surgery. Also, since it uses a natural body orifice instead of incisions to enter the body, it may result in reduced needs for general anesthetics and faster recovery times.

Medical robotic systems such as these generally require surgical instruments that are capable of cutting, grasping, and suturing tissue to perform medical procedures. However, in endoluminal devices which include integrated surgical instruments and an image capturing device, it may be difficult to ensure that the surgical instruments implemented therein can always generate sufficient cutting force or adequate dexterity to accomplish their intended tasks. Further, due to the nature of such robotically controlled instruments, their manipulation may be difficult to master for users of the medical robotic systems.

OBJECTS AND SUMMARY OF THE INVENTION

Accordingly, one object of one or more aspects of the present invention is a medical device to be used in a medical robotic system that is easy for an operator to use for performing a medical procedure at a surgical site within a patient.

Another object of one or more aspects of the present invention is a medical device to be used in a medical robotic system that does not require the need to generate large forces at its tip to perform its intended task at a surgical site within a patient.

Still another object of one or more aspects of the present invention is a medical device to be used in a medical robotic system that does not interfere with a camera's view while being used during the performance of a medical procedure at a surgical site within a patient.

Yet another object of one or more aspects of the present invention is a medical device to be used in a medical robotic system that may be accurately and reliably used during the performance of a medical procedure at a surgical site within a patient.

These and additional objects are accomplished by the various aspects of the present invention, wherein briefly stated, one aspect is a medical robotic system comprising: an input device; a manipulator; a medical device coupled to the manipulator, the medical device having a conduit and an orientable tip, the orientable tip having a proximal end coupled to a distal end of the conduit; a catheter extending through the conduit and to a distal end of the orientable tip; a biomaterial source coupled to a proximal end of the catheter; and a processor configured to command the manipulator to manipulate the orientable tip so as to point a distal end of the catheter according to operator manipulation of the input device.

Another aspect is a method for configuring a medical device for performing a medical procedure using a medical robotic system, comprising: inserting a catheter through a conduit of the medical device so as to extend to a distal end of an orientable tip of the medical device; coupling a biomaterial source to a proximal end of the catheter; and coupling the medical device to the medical robotic system so that a position and orientation of a distal end of the catheter is controllable by controlling a position and orientation of the orientable tip through operator manipulation of an input device.

Another aspect is a medical device couplable to a medical robotic system, comprising: a conduit; a hollow tip; a wrist mechanism coupling the hollow tip to the conduit so that respective passages in the conduit and the hollow tip are aligned; and an interface coupled to the wrist mechanism and adapted to couple to the medical robotic system so that the medical robotic system controls movement of the wrist mechanism according to operator manipulation of an input device of the medical robotic system.

Still another aspect is a method for using method for using a medical device in a medical robotic system, comprising: robotically manipulating a tip of the medical device so as to point towards a target tissue while activating a laser beam through an optical fiber extending through the medical device to a distal end of the tip so as to selectively sever a portion of the target tissue; and robotically manipulating the tip of the medical device so as to point towards the target tissue while selectively applying first and second biomaterials through separate lumens of a catheter extending through the medical device to the distal end of the tip so as to selectively apply a mixture of the first and second biomaterials to a non-severed portion of the target tissue.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
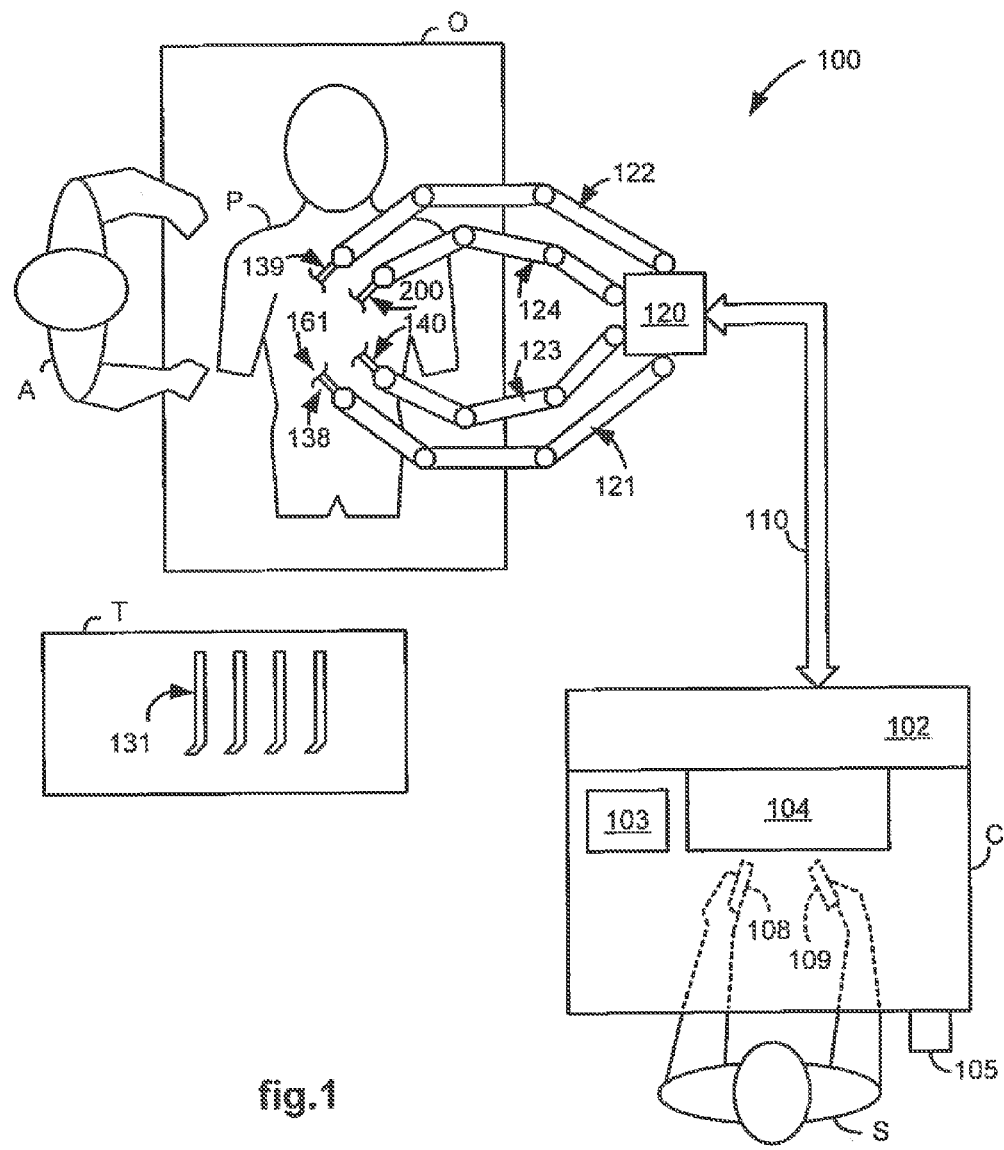
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console C utilized by a Surgeon S while performing a medical procedure, such as a diagnostic or surgical procedure, with assistance from one or more Assistants A, on a Patient P who is lying down on an Operating table O.

The Console includes a monitor 104 for displaying a three-dimensional ("3-D") image of a surgical site to the Surgeon, a processor 102, a microphone 103, a foot pedal 105, and left and right manipulatable input devices 108, 109. The input devices 108, 109 may include any one or more of a variety of control devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the System 100.

The Console is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote medical procedures.

The Surgeon performs the medical procedure by manipulating the input devices 108, 109 so that the processor 102 causes associated ones of the robotic arms 121, 122, 123, 124 to move their respective removably coupled medical devices 138, 139, 140, 200 while the Surgeon views the surgical site on the Console monitor 104 as it is captured by an image capturing device 140. For example, robotic arms 121, 122 and their respective medical devices 138, 139, which are surgical instruments, may be associated at one time during the medical procedure with the input devices 108, 109 so that the surgical instruments 138, 139 may be robotically moved by the Surgeon manipulating the input devices 108, 109. At another time during the medical procedure, robotic arm 123 and its medical device 140, which is a stereoscopic endoscope, may be associated with one of the input devices 108, 109 so that the endoscope 140 can be properly positioned to view the medical procedure by the Surgeon manipulating its associated input device. At still another time during the medical procedure, robotic arm 124 and its medical device 200, which provides laser cutting and/or biomaterial application capability, may be associated with one of the input devices 108, 109 so that the medical device 200 may be robotically moved by the Surgeon manipulating its associated input device.

Each of the medical devices 138, 139, 140, 200, is conventionally inserted through a tool guide (not shown) into the Patient so as to extend down to the surgical site through a corresponding minimally invasive incision such as Incision 161. The number of medical devices used at one time and consequently, the number of robotic arms being used in the system 100 will generally depend on the medical procedure being performed and the space constraints within the operating room, among other factors. If it is necessary to change a medical device being used during a procedure, the Assistant may remove the medical device no longer being used from its robotic arm, and replace it with another medical device 131 from a Tray T in the operating room.

Each of the robotic arms 121, 122, 123, 124 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arms 121, 122, 123, 124 so that their respective medical devices may be inserted into their respective tool guides. The robotic arms 121, 122, 123, 124 are attached to a patient-side cart 120 having wheels for easily moving it from one location to another.

The input devices 108, 109 are provided with at least the same degrees of freedom as their associated medical devices to provide the Surgeon with telepresence, or the perception that the input devices 108, 109 are integral with their associated medical devices so that the Surgeon has a strong sense of directly controlling the medical devices. Accordingly, position, force, and tactile feedback sensors are preferably employed on the medical devices to transmit position, force, and tactile sensations from the medical devices back to the Surgeon's hands as he/she operates the input devices 108, 109. Tactile feedback is especially useful when the medical devices being controlled are the surgical instruments 138, 139.

Preferably, the monitor 104 is positioned near the Surgeon's hands so that it will display a projected image that is oriented so that the Surgeon feels that he or she is actually looking directly down onto the operating site. Accordingly, images of the surgical instruments 138, 139 appear to be located substantially where the Surgeon's hands are located when they are associated with the input devices 108, 109. In addition, the real-time image is projected into a perspective image such that the Surgeon can manipulate the end effectors of the surgical instruments 138, 139 through their associated input devices 108, 109 as if viewing the workspace in substantially true presence. By true presence, it is meant that the presentation of an image is a true perspective image simulating the viewpoint of an operator that is physically manipulating the surgical instruments 138, 139. Thus, the processor 102 transforms the coordinates of the surgical instruments 138, 139 to a perceived position so that the perspective image is the image that one would see if the endoscope 140 was located directly behind the surgical instruments 138, 139.

The processor 102 performs various functions in the system 100 including the performance of certain methods described herein. One important function that it performs is to translate and transfer the mechanical motion of input devices 108, 109 to the slave manipulators of associated robotic arms through control signals over bus 110 so that the Surgeon can effectively manipulate their respective medical devices.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on the construction and operation of a medical robotic system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

Figure 2:
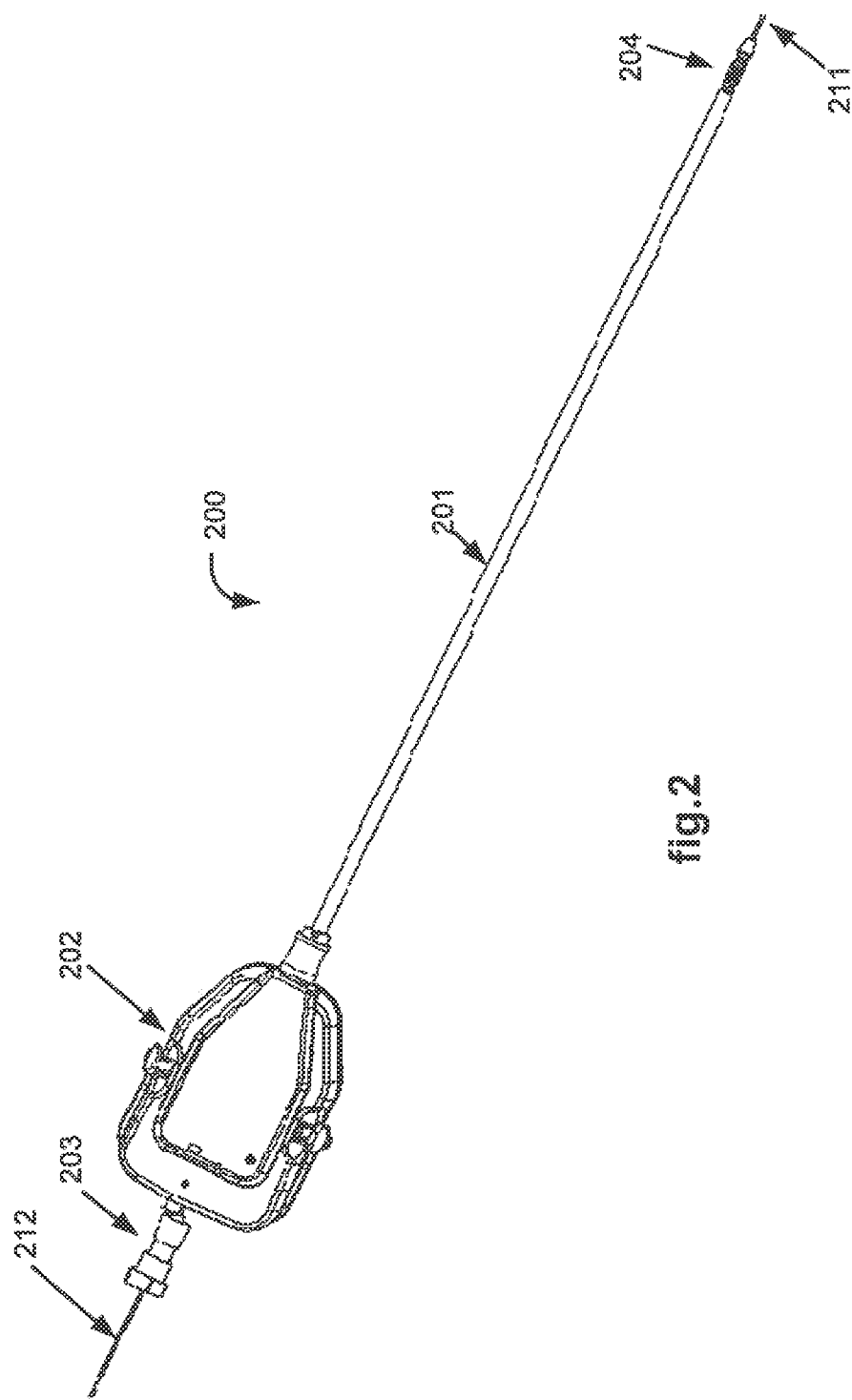
FIG. 2 illustrates a top view of a medical device utilizing aspects of the present invention.

FIG. 2 illustrates, as an example, one embodiment of the medical device 200 which provides optical laser and/or biomaterial application capability. The laser may be used for many purposes such as cutting, coagulation, ablation, illumination, and other known medical uses for lasers. Laser cutting provides a number of advantages over conventional cutting tools such as scissors and scalpels attached as end effectors to medical devices, such as the surgical instruments 138, 139. First of all, it may be difficult to generate sufficient cutting or shearing forces for such scissors and scalpel tools in a minimally invasive robotic surgical system (or endoluminal device), and laser cutting eliminates the need for the generation of such forces. Secondly, it may be difficult for the Surgeon to learn to use such scissors and scalpel tools in an endoluminal robot since the Surgeon must manipulate them from a flexible robotic platform and therefore, generally may have to do so with reduced degrees of freedom and sensory control. In contrast, learning to simply direct a tip of a medical device with laser cutting capability is presumably easier to learn and more accurate for cutting.

The capability to easily and accurately apply biomaterials (such as those having hemostatic, adhesive, or adhesion barrier characteristics) to targeted tissue is also useful during or after the performance of a medical procedure on a patient using a minimally invasive robotic surgical system (or endoluminal device). The capability to apply biomaterials having adhesive characteristics is particularly useful as an alternative to suturing.

For example, BioGlue® Surgical Adhesive ("BioGlue"), a surgical adhesive product of CryoLife, Inc. of Kennesaw, Ga., is delivered as a two part liquid (49% concentrated bovine serum albumin and 10% glutaraldehyde) that rapidly polymerizes after mixing to form an impermeable seal on tissue. BioGlue is characterized by a quick bonding time independent of the body's clotting mechanisms. Upon mixing, the two components cross-link to each other and to cell surface proteins and extracellular matrix proteins at the repair site of application. It begins to bond within 20 to 30 seconds of mixing and reaches its maximal bonding capability in two minutes, creating a flexible mechanical seal.

Another biomaterial mixture having hemostatic and/or adhesive qualities is fibrin, which is applied as a two-component mixture in which a solution of concentrated fibrinogen and factor XIII are combined with a solution of thrombin and calcium in order to form a coagulum, simulating the final stage of the clotting cascade. Once mixed, a fibrin clot forms in a few seconds, or somewhat slower if a more dilute form of thrombin is used. In some preparations, or in selected indications, an antifrinolytic agent (aprotinin) is included to prevent lysis of the clot.

The medical device 200 comprises a conduit 201 having one or more passages through which an optical fiber and/or a multi-lumen catheter for applying biomaterials may be removably inserted, an interface 202 for interfacing with the robotic arm 124 to which the medical device 200 is mechanically and electrically coupled, a mechanical coupler 203 for holding the inserted optical fiber and/or multi-lumen catheter, and an orientable tip 204 which is mechanically coupled to the interface 202 so that it may be robotically controlled to bend in different directions in response to operator manipulation of an associated one of the input devices 108, 109. Proximal end(s) 212 of the inserted optical fiber and/or multi-lumen catheter extend out of the interface 202 at one end of the medical device 200, and distal end(s) 211 of the inserted optical fiber and/or multi-lumen catheter extend to an open end of the orientable tip 204 at the other end of the medical device 200.

Figure 3:
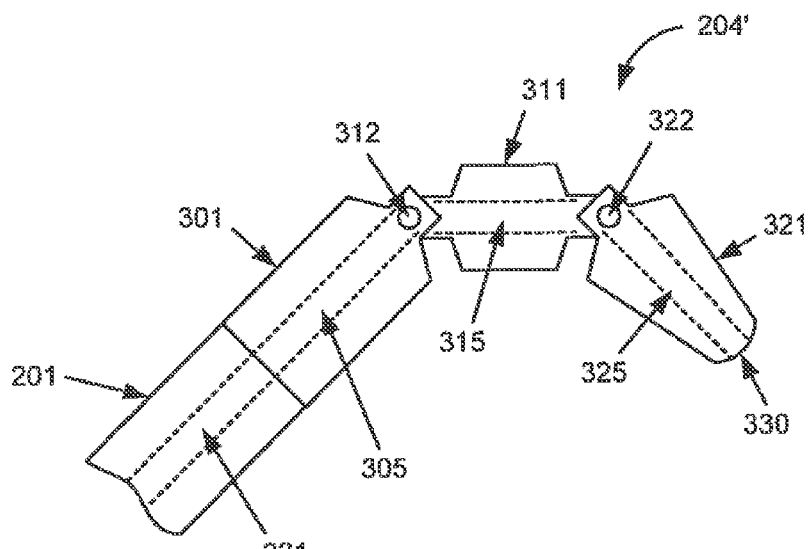
FIG. 3 illustrates a side view of a simple two-jointed tip of a medical device utilizing aspects of the present invention.

FIG. 3 illustrates, as an example, a simple two joint orientable tip 204' that is controllably orientable in pitch and roll angular directions about a longitudinal axis of the conduit 201. A first section 301 couples to a distal end of the conduit 201 so that it rotates when the conduit 201 is rotated by its robotic arm 124 to provide a controllable 360 degree roll angular movement. Section 321 is controllably pivotable about joint 322 by at least ±45 degrees and likewise, section 311 is controllably pivotable about joint 312 by at least ±45 degrees. As a result, the distal end of the tip 204 is orientable by approximately ±90 degrees or more about the joint 312 in the pitch angular direction relative to the longitudinal axis of the conduit 201. Thus, the orientable tip 204' comprises three sections 301, 311, 321 which operate as a "wrist" mechanism that allows controlled pointing of the tip 204' within a cone-like area having a vertex at the pivot joint 312 and a central axis along the longitudinal axis 501 of the conduit 201.

When the orientable tip 204' is coupled to the conduit 201, defined passages 305, 315, 325 within the sections 301, 311, 321 of the tip 204' align with corresponding passages 221 of the conduit 201 so that an optical fiber and/or multi-lumen catheter extending through the passages 221 of the conduit 201 may pass through the passages 305, 315, 325 of the orientable tip 204' to a distal end 330 of the tip 204'.

Figure 4:
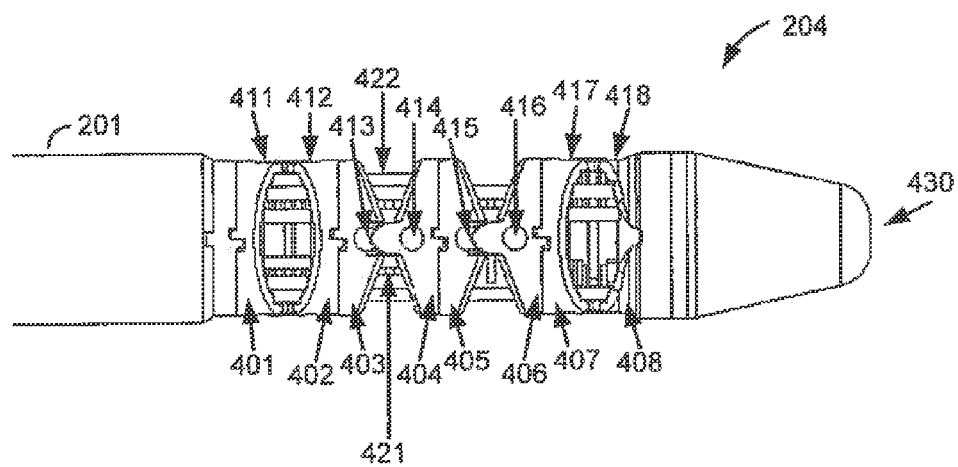
FIG. 4 illustrates a side view of a multi-jointed tip of a medical device utilizing aspects of the present invention.

FIG. 4 illustrates, as a more sophisticated example, a four joint orientable tip 204 that is controllably orientable in pitch, roll and yaw angular directions relative to the longitudinal axis of the conduit 201. In this example, four sections are shown, each comprising a pair of disk segments pivotably coupled together by an intervening strut. The first and fourth sections provide controllable yaw angular movement, and the second and third sections provide controllable pitch angular movement. The tip 204 is coupled to a distal end of the conduit 201 so that it rotates when the conduit 201 is rotated by its robotic arm 124 to provide controllable 360 degree roll angular movement.

The second section includes disk segments 403, 404 and dual pivots 413, 414, which provide at least ±45 degrees controllable pitch angular movement about one or the other of the pivots 413, 414. Similarly, the third section includes disk segments 404, 405 and dual pivots 415, 416 which provide at least ±45 degrees controllable pitch angular movement about one or the other of the pivots 415, 416. As a result, the distal end of the tip 204 is controllably orientable by at least ±90 degrees about one or the other of the pivots 413, 414 in the pitch angular direction relative to the longitudinal axis of the conduit 201.

The first and fourth sections are 90 degrees offset (i.e., rotated approximately 90 degrees in the roll direction relative to the longitudinal axis of the conduit 201) from the first and fourth sections. The first section includes disk segments 401, 402 and dual pivots 411, 412 (not seen because of their 90 degree offset from dual pivots 413, 414) which provide at least ±45 degrees controllable yaw angular movement about one or the other of the pivots 411, 412. Similarly, the fourth section includes disk segments 407, 408 and dual pivots 417, 418 (not seen because of their 90 degree offset from dual pivots 415, 416) which provide at least ±45 degrees controllable yaw angular movement about one or the other of the pivots 417, 418. As a result, the distal end of the tip 204 is controllably orientable by at least ±90 degrees about one or the other of the pivots 411, 412 in the yaw angular direction relative to the longitudinal axis of the conduit 201.

Cables 421, 422 extend from a conventional motor driven pulley arrangement (not shown) in the interface 202 to the disk segment 404 so that by pulling one or the other of the cables 421, 422, the disk segment 404 may be pivoted about the pivots 413, 414 in one direction or the other. Similarly, other cable pairs (not shown) extend from other conventional motor driven pulley arrangements (not shown) in the interface 202 to their respective disk segments so that by pulling one or the other of the cables in the pair, the disk segment may be pivoted about its pivot joint in one direction or the other.

As in the tip 204' described in reference to FIG. 3 above, passages (not shown) are defined within the sections of the tip 204 so as to align with corresponding passages 221 of the conduit 201 so that an optical fiber and/or multi-lumen catheter extending through the passages 221 of the conduit 201 may pass through the section passages to a distal end 430 of the orientable tip 204.

The dual pivots of each section of the tip 204 are coupled through the section's strut so that "cable balancing" is achieved wherein the cable length paid out on one side is equal to the cable length pulled on the other side of the disk segment. For additional details on such "cable balancing" and the construction and operation of the wrist mechanism of the orientable tip 204, as well as the construction and operation of other wrist mechanisms that may be alternatively used in the tip 204, see commonly owned U.S. Pat. No. 6,817,974, "Surgical Tool having Positively Positionable Tendon-Actuated Multi-Disk Wrist Joint," which is incorporated herein by reference.

Figure 5:
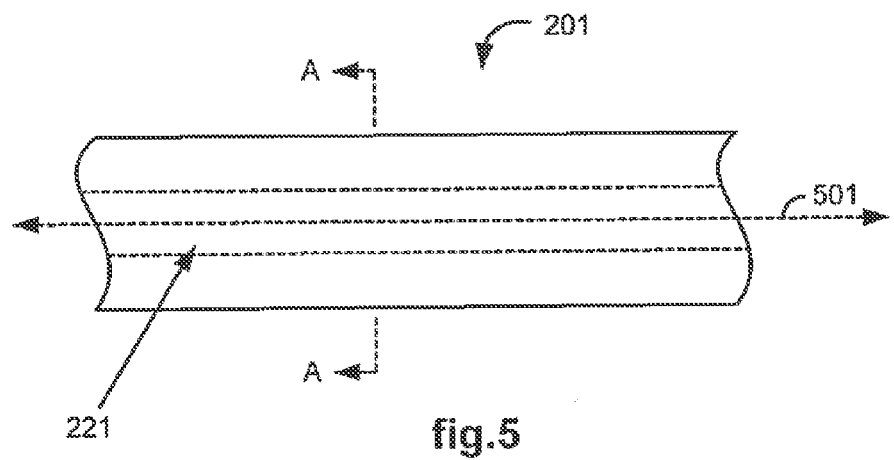
FIG. 5 illustrates a side view of a conduit of a medical device utilizing aspects of the present invention.
Figure 6:
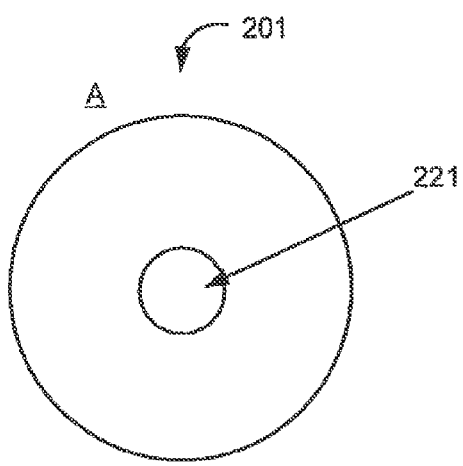
FIG. 6 illustrates a cross-sectional view of a single-passage conduit of a medical device utilizing aspects of the present invention.
Figure 7:
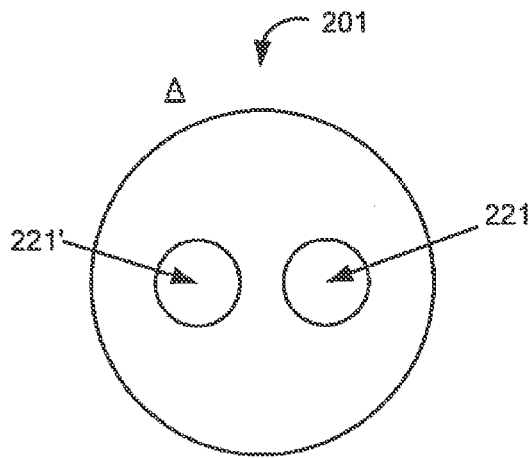
FIG. 7 illustrates a cross-sectional view of a dual-passage conduit of a medical device utilizing aspects of the present invention.

FIGS. 5~7 illustrate examples of one or more passages 221 extending through and along the length of the conduit 201. In the case where only one passage 221 is provided, the passage 221 may be centered in the conduit so that its central axis aligns with the central axis 501 of the conduit 201 (as shown in partial side view of the conduit 201 in FIG. 5 and cross-sectional view of the conduit 201 in FIG. 6). In this case, an optical fiber and multi-lumen catheter may take turns being inserted in the single passage 221 so that each only resides in the passage 221 when it is needed and is removed when not needed.

On the other hand, in the case where two passages 221 are provided, the passages 221 may be vertically centered and horizontally side-by-side so that their central axes are parallel with the central axis 501 of the conduit 201 (as shown in partial side view of the conduit 201 in FIG. 5 and cross-sectional view of the conduit 201 in FIG. 7). In this case, both passages 221 may be used at the same time with the optical fiber in one and the multi-lumen catheter in the other. Other shapes, sizes, numbers and geometrical arrangements of passages 221 may also be implemented in the medical device 200, and are fully contemplated as being within the full scope of the present invention.

Figure 8:
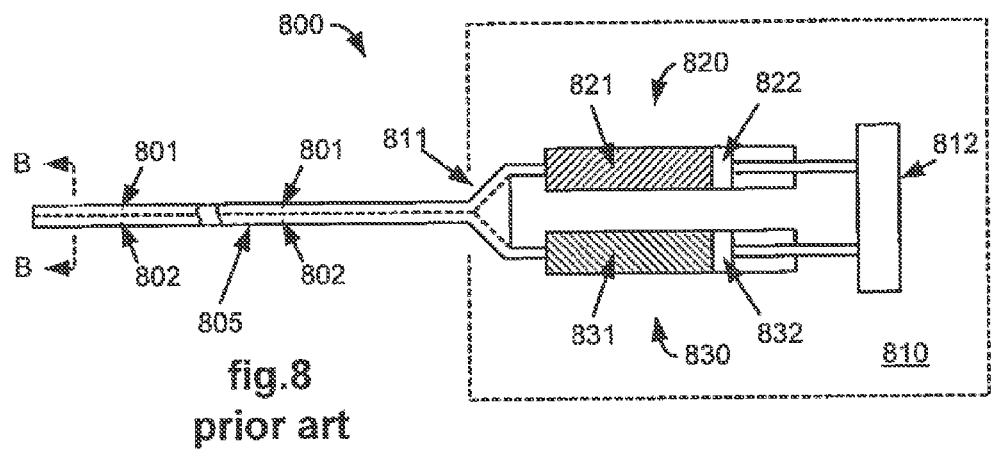
FIG. 8 illustrates a top view of a prior art biomaterial applicator included in a medical device utilizing aspects of the present invention.
Figure 9:
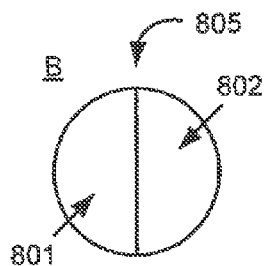
FIG. 9 illustrates a cross-sectional view of a dual-lumen catheter of a prior art biomaterial applicator included in a medical device utilizing aspects of the present invention.

FIG. 8 illustrates, as an example, a top view of a biomaterial applicator 800 which includes a multi-lumen catheter 805 and a syringe assembly 810, and FIG. 9 illustrates, as an example, a cross-sectional view of the multi-lumen catheter 805. A biomaterial applicator such as described in reference to FIGS. 8~9 is commercially available from Micromedics, Inc. of St. Paul, Minn.

The syringe assembly 810 includes a first syringe 820 which may be filled with a first biomaterial 821 and a second syringe 830 which may be filled with a second biomaterial 831. A V-shaped neck 811 couples the first and second syringes 820, 830 respectively to the first and second lumens

801, 802 of the catheter 805. A connecting structure 812 couples together first and second plungers 822, 832 of the first and second syringes 820, 830 so that when the connecting structure 812 is moved towards the catheter 805, the first and second plungers 822, 832 move accordingly to force the first and second biomaterials 821, 831 through the first and second lumens 801, 802 of the catheter 805. The first and second biomaterials 821, 831 forced out of the distal end of the catheter 805 then form a mixture upon their exits of the first and second lumens 801, 802 of the catheter 805, such as in the case of BioGlue® or fibrin.

Figure 10:
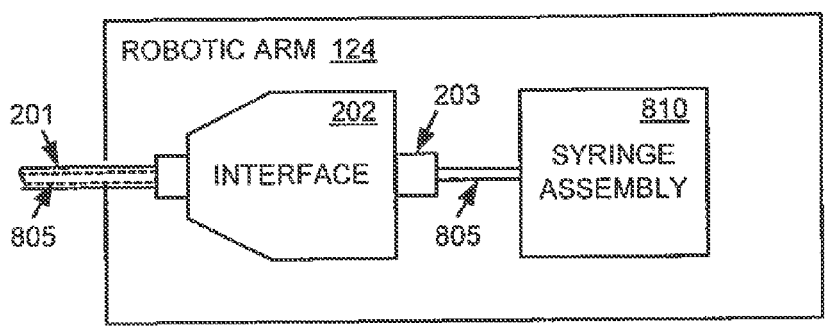
FIG. 10 illustrates a simplified top view of a robotic arm with attached biomaterial applicator medical device utilizing aspects of the present invention.

FIG. 10 illustrates, as an example, a simplified view of the robotic arm 124 with the biomaterial applicator 800 inserted into the medical device 200 by passing the catheter 805 of the biomaterial applicator 800 through the interface 202 and conduit 201 of the medical device 200 until a distal end of the catheter 805 exits a distal end of the orientable tip 204 of the medical device 200, and securing the biomaterial applicator 800 in that position by using the coupler 203. After using the biomaterial applicator 800, it may be removed from the medical device 200 by releasing the coupler 203, and extracting the catheter 805 from the conduit 201 and interface 202 of the medical device 200. The biomaterial applicator 800 may then be cleaned and reused at a later time, or it may be disposed of. Thus, the biomaterial applicator 800 is a removably disposable component of the medical device 200.

Figure 11:
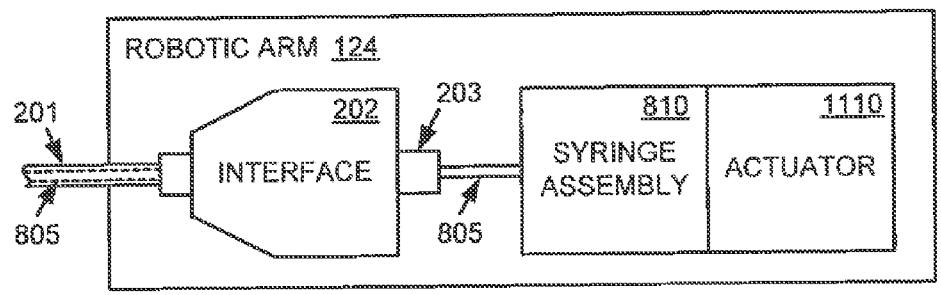
FIG. 11 illustrates a simplified top view of a robotic arm with attached and remotely actuatable biomaterial applicator medical device utilizing aspects of the present invention.

FIG. 11 illustrates, as an example, a simplified view of the robotic arm 124 with the biomaterial applicator 800 inserted into the medical device 200, as described in reference to FIG. 10, with an actuator 1110 coupled to the connecting structure 812 of the biomaterial applicator 800 so as to be capable of moving the plungers 822, 832 to expel the first and second biomaterials 821, 831 out of the first and second lumens 801, 802 of the catheter 805 of the biomaterial applicator 800 when commanded to do so by, for example, the Surgeon depressing a designated button on one of the input devices 108, 109 associated at the time with the medical device 200. Note that if such an actuator is not provided, as in the case with the configuration shown in FIG. 10, the connecting structure 812 of the biomaterial applicator 800 may still be manually actuated by an Assistant, who is positioned near the robotic arm 124, at the request of the Surgeon communicating with the Assistant either directly if he is within hearing distance, or from a distance using the microphone 103 and a speaker (not shown) located within the Assistant's hearing distance.

Figure 12:
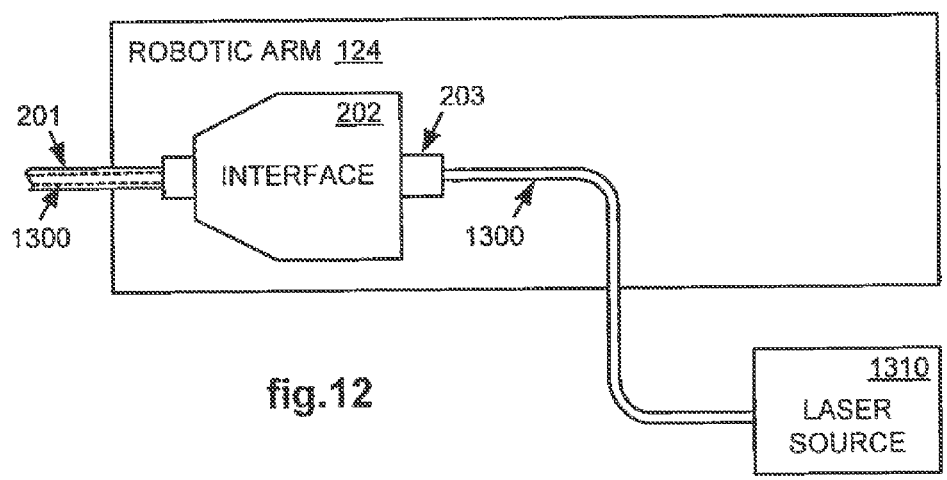
FIG. 12 illustrates a simplified top view of a robotic arm with attached laser cutting medical device utilizing aspects of the present invention.

FIG. 12 illustrates, as an example, a simplified view of the robotic arm 124 with an optical fiber 1300 inserted into the medical device 200 by passing the optical fiber 1300 through the interface 202 and conduit 201 of the medical device 200 until a distal end of the optical fiber 1300 exits a distal end of the orientable tip 204 of the medical device 200, and securing the optical fiber 1300 in that position by using the coupler 203. The optical fiber 1300 is connected to a laser source 1310 so that a laser beam may be directed out of the distal end of the optical fiber 1300 upon activation of the laser source 1310 by, for example, the Surgeon depressing a designated button on one of the input devices 108, 109 associated at the time with the medical device 200. After using the optical fiber 1300, it may be removed from the medical device 200 by releasing the coupler 203, and extracting the optical fiber 1300 from the conduit 201 and interface 202 of the medical device 200.

Figure 13:
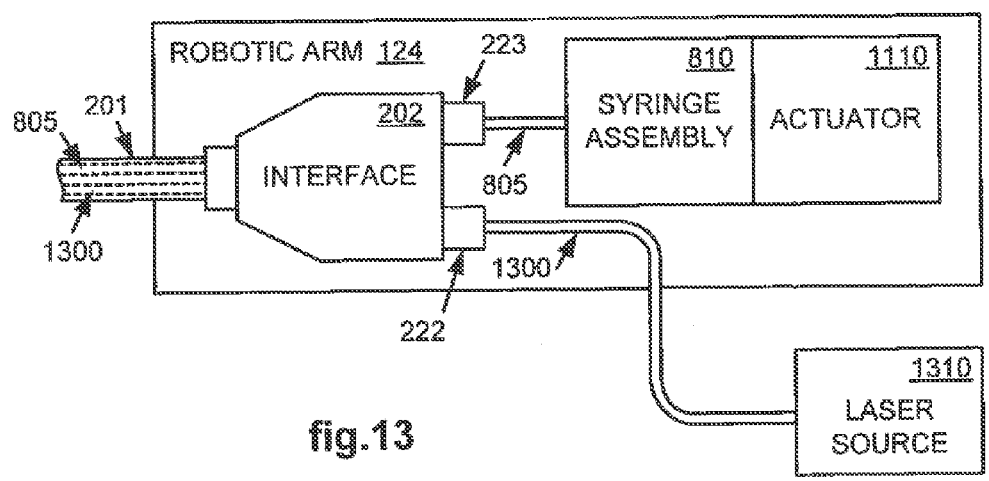
FIG. 13 illustrates a simplified top view of a robotic arm with attached laser cutting and remotely actuatable biomaterial applicator medical device utilizing aspects of the present invention.

FIG. 13 illustrates, as an example, a simplified view of the robotic arm 124 with both the optical fiber 1300 and the biomaterial applicator 800 inserted into the medical device 200. In this case, the conduit 201 of the medical device 200 has first and second passages 221, for example, such as shown in FIG. 7, with the optical fiber 1300 extending through the first passage and the catheter 805 of the biomaterial applicator 800 extending through the second passage. Separate couplers 222, 223 are provided to respectively secure the catheter 805 and the optical fiber 1300 once they have been properly inserted as described in reference to FIGS. 10 and 12. Extraction of the optical fiber 1300 and catheter 805 may also be performed as described in reference to FIGS. 10 and 12 after releasing their respective couplers 222, 223.

Figure 14:
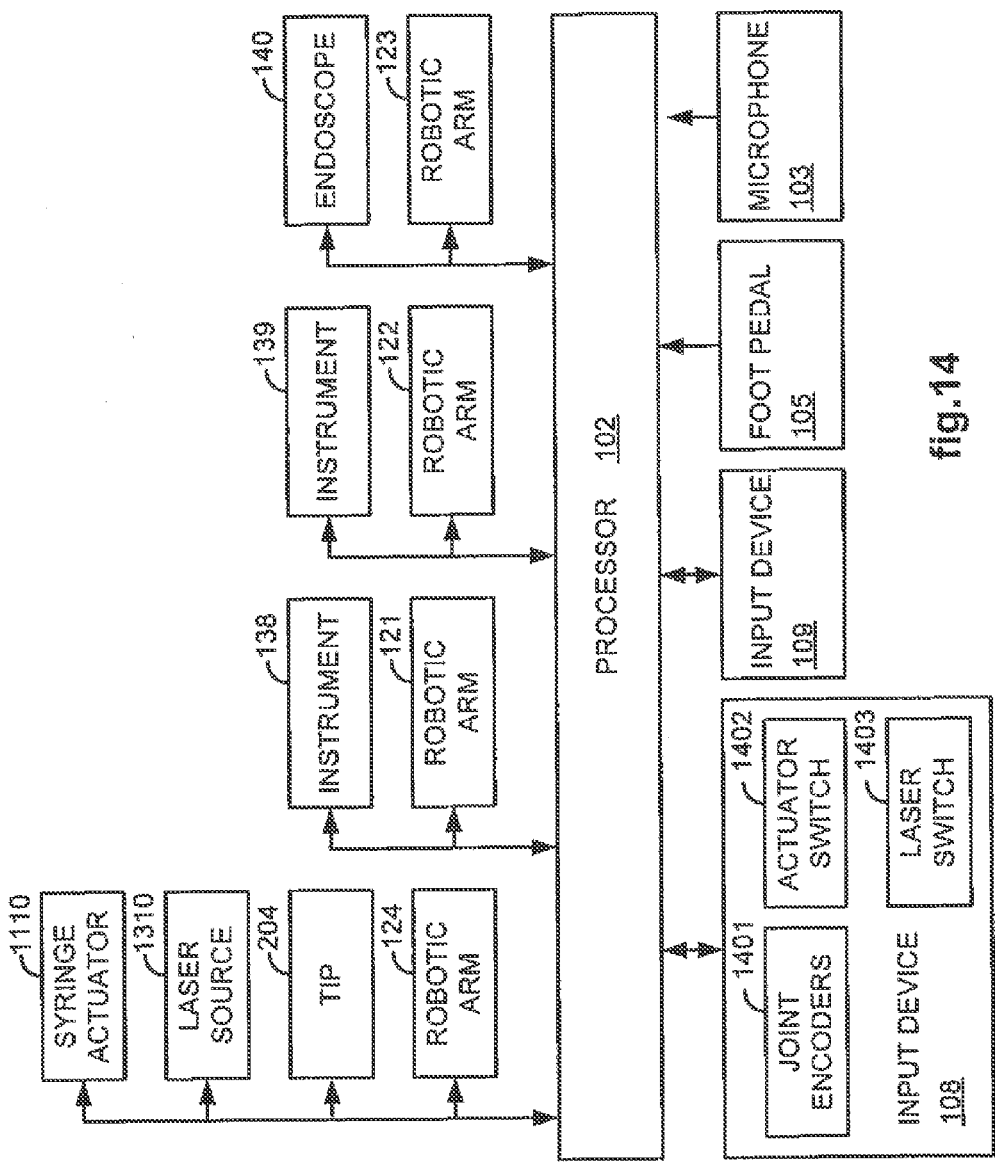
FIG. 14 illustrates a block diagram of medical robotic system including a laser cutting and remotely actuatable biomaterial applicator medical device utilizing aspects of the present invention.

FIG. 14 illustrates, as an example, a block diagram of the medical robotic system 100, which is adapted with a laser cutting (and other purposes) and remotely actuatable biomaterial applicator medical device 200 such as shown and described in reference to FIG. 13. The input device 108 may be selectively associated with the robotic arm 124 holding the medical device 200 or the robotic arm 121 holding the surgical instrument 138. The Surgeon may select which robotic arm is to be associated with which input device by using a pointing device (not shown) and a Graphical User Interface ("GUI") associated with the monitor 104. Alternatively, the Surgeon may perform such selection by speaking commands into the microphone 103 that are recognized by voice recognition software being executed by the processor 102. In either case, the processor 102 performs the association by transmitting command information from the input device to the associated robotic arm and its attached medical device.

When the Surgeon moves the input device 108, the movement is detected by joint encoders 1401 in the input device 108. The joint encoders 1401 provide the movement information to the processor 102, which converts the information into commands transmitted over the bus 110 to move the medical device 200 and/or its tip 204 accordingly. For example, movement of the medical device 200 may be effected by commanding the robotic arm 124 to move the medical device 200 as desired, and movement of the orientable tip 204 of the medical device 200 may be effected by commanding motor driven pulley arrangements in the interface 202 of the medical device 200 to be actuated as described in reference to FIGS. 3 and 4.

After the Surgeon has positioned the medical device 200 at a proper distance from a target tissue and directed its tip 204 so as to point towards the target tissue by moving the input device 108, the Surgeon may then perform either laser or biomaterial application on the target tissue. For example, if laser cutting is to be performed on the target tissue, then the Surgeon may activate a laser switch 1403 (such as a thumb depressible button on the input device 108, a foot switch on the foot pedal 105, or a voice command spoken into the microphone 103 that is recognized by voice recognition software implemented in the processor 102) that causes the laser source 1310 to be turned on, while moving the input device 108 with his or her hand so as to cause the tip 204 of the medical device 200, and consequently, a laser beam emanating from the optical fiber 1300 coupled to the laser source 1310, to be directed to the area of the target tissue to be cut.

On the other hand, if biomaterial application is to be performed on the target tissue, then the Surgeon may activate an actuator switch 1402 (such as a thumb depressible button on the input device 108, a foot switch on the foot pedal 105, or a voice command spoken into the microphone 103 that is recognized by voice recognition software implemented in the processor 102) that causes the syringe actuator 1110 to force biomaterials concurrently out of the first and second syringes 820, 830 so as to form a biomaterial mixture as they are expelled out of the first and second lumens 801, 802 of the catheter 805, while moving the input device 108 with his or her hand so as to cause the tip 204 of the medical device 200, and consequently, the biomaterial mixture being emitted from the catheter 805, to be directed to the area of the target tissue upon which the biomaterial mixture is to be applied.

Figure 15:
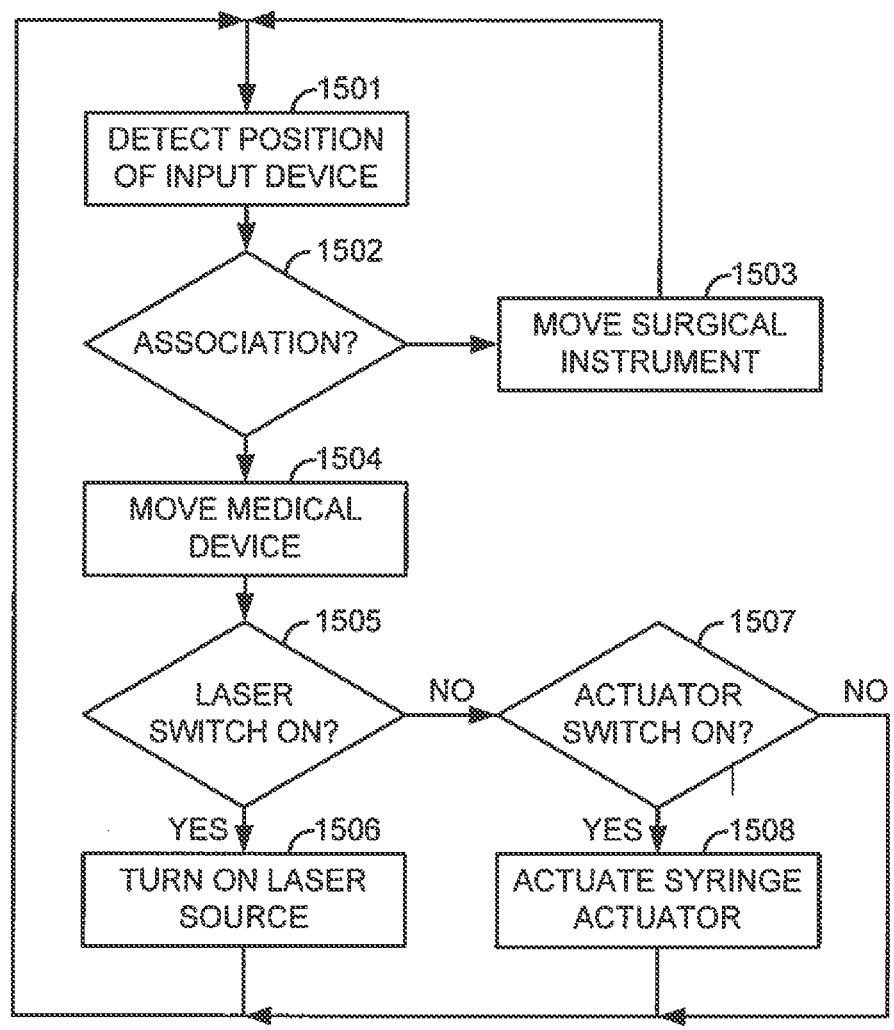
FIG. 15 illustrates a flow diagram of a method for performing laser cutting and biomaterial application on target tissue, utilizing aspects of the present invention.

FIG. 15 illustrates, as an example, a flow diagram of a method utilizing the processor 102 for performing laser cutting and biomaterial application on target tissue. In 1501, a position (and/or movement) of the input device 108 is detected by the processor 102 (e.g., from information provided by the joint encoders 1401 in the input device 108). In 1502, a determination is made whether the input device 108 is presently associated with the robotic arm 121 (to which the surgical instrument 138 is coupled) or the robotic arm 124 (to which the medical device 200 is coupled). If the input device 108 is presently associated with the robotic arm 121, then in 1503, the processor 102 causes the robotic arm 121 and/or an end effector of its coupled surgical instrument 138 to be moved accordingly. On the other hand, if the input device 108 is associated with the robotic arm 124, then in 1504, the processor 102 causes the robotic arm 124 and/or the tip 204 of its coupled medical device 200 to be moved accordingly. Note that if the input device 108 is not a shared input device (e.g., it is configured to be fixedly associated with the robotic arm 124 of the medical device 200), then 1502 and 1503 are unnecessary, and the method proceeds directly from 1501 to 1504.

After or concurrently with the movement commanded in 1504, a determination is made in 1505 whether the laser switch 1403 is activated (e.g., whether a thumb depressible button on the input device 108 is being depressed at the time). If the determination in 1505 is YES, then in 1506, the laser source 1310 is turned ON, and the method loops back to 1501 to detect and process a subsequent position (and/or movement) of the input device 108. On the other hand, if the determination in 1505 is NO, then the method proceeds to 1507.

In 1507, a determination is made whether the actuator switch 1402 is activated (e.g., whether another thumb depressible button on the input device 108 is being depressed at the time). If the determination in 1507 is YES, then in 1508, the syringe actuator 1110 is actuated, and the method loops back to 1501 to detect and process a subsequent position (and/or movement) of the input device 108. On the other hand, if the determination in 1507 is NO, then the method loops back to 1501 without actuating the syringe actuator 1110.

Note that although the description above in reference to FIG. 15 indicates that the method determines whether the laser switch 1403 is activated before determining whether the actuator switch 1402 is activated, it is to be appreciated that the order of such determinations may be reversed or the determinations may be made concurrently. Further, if an optical fiber has not been inserted in the medical device 200, then the determination made in 1505 may be skipped altogether. Similarly, if a catheter of a biomaterial applicator has not been inserted in the medical device 200, then the determination made in 1507 may be skipped altogether.

Also, although the use of laser and actuator switches 1403, 1402 included in the input device 108 are described herein for activating laser cutting and biomaterial application, it is to be appreciated that other activation techniques may be used, such as, for example, voice activation using the microphone 103 and conventional voice recognition software executed by the processor 102. In the case of voice activation, when the voice recognition software recognizes the Surgeon's voice command to activate laser cutting, it may set a laser flag stored in the memory of the processor 102, so that in 1505, the processor 102 would check the status of the laser flag instead of whether the laser switch described therein has been switched on. Similarly, when the voice recognition software recognizes the Surgeon's voice command to activate biomaterial application, it may set an actuator flag stored in the memory of the processor 102, so that in 1507, the processor 102 would check the status of the actuator flag instead of whether the actuator switch described therein has been switched on.

A laser and biomaterial applying medical device employing aspects of the present invention as described herein is useful in a number of applications. For example, in "transgastric" surgery where an endoluminal device may be passed through the mouth and into the stomach of the Patient, the Surgeon may use the laser cutting capability to cut a hole in the stomach wall so that the endoluminal device may enter the abdominal cavity and perform a medical procedure therein. Once the medical procedure is completed, the endoluminal device may be withdrawn from the abdominal cavity and the Surgeon may then use the biomaterial applicator capability to seal the hole previously cut in the stomach wall. Other applications involving cutting or severing diseased tissue for removal from adjoining tissue and adhering the non-severed adjoining tissue back together (such as in a coronary artery bypass procedure) may also be performed using the medical device 200 in conjunction with surgical instruments having grasping end effectors (or a flexible endoluminal device incorporating aspects of the present invention as described herein in reference to the medical device 200).

Figure 16:
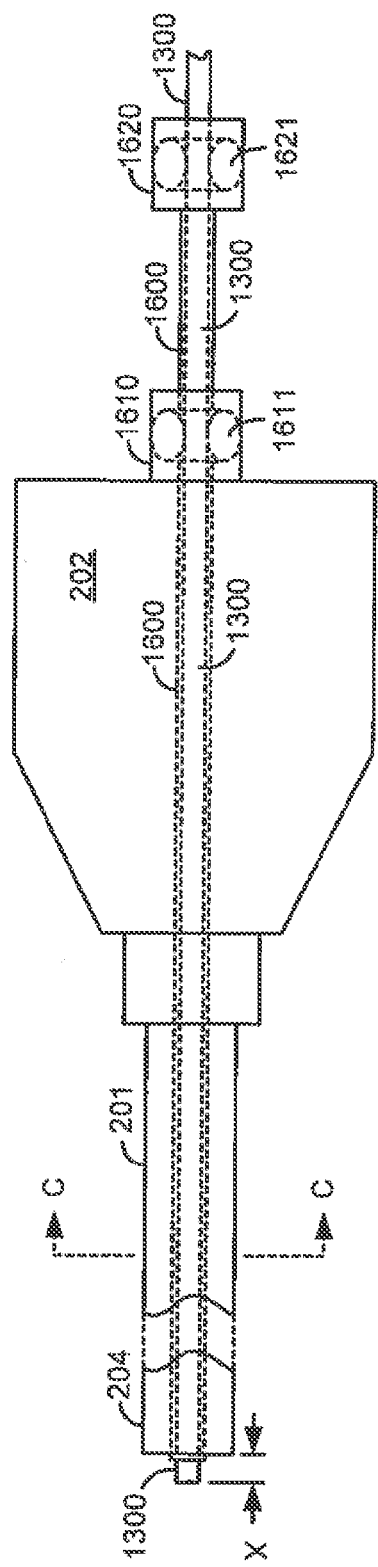
FIG. 16 illustrates a simplified top view of a medical device with dual couplers for coupling a sheathed optical fiber to the medical device, utilizing aspects of the present invention.

Although a single coupler 203 is shown in FIG. 12 for coupling the optical fiber 1300 to the interface 202 of the medical device 200, a dual coupler scheme, such as shown in FIG. 16, may better secure the optical fiber 1300 when placed within a protective sheath 1600 passing through the shaft 201 of the medical device 200 during its use in a medical procedure. A similar dual coupler scheme may also be used for attaching the biomaterial applicator 800 to the medical device 200 when its catheter 805 is sheathed.

Figure 17:
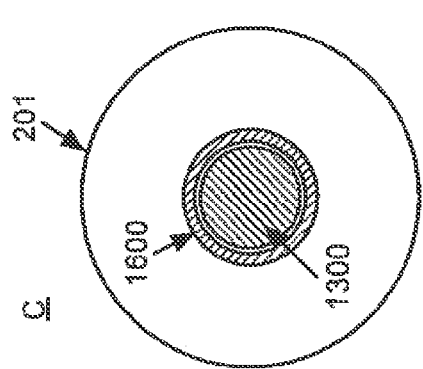
FIG. 17 illustrates a cross-sectional view of a conduit of a medical device, utilizing aspects of the present invention, with a sheathed optical fiber extending through a passage of the conduit.

Referring to FIG. 16, the sheath 1600 is a long flexible tube that is inserted into a proximal end of the interface 202 and passed through the interface 202 and the shaft 201 until a distal end of the sheath 1600 exits the tip 204 of the medical instrument 200. The optical fiber 1300 is then inserted through the protective sheath 1600 until it also exits and extends out of the tip 204 by a workable amount designated as the distance "X". FIG. 17 illustrates a cross-sectional view cut along line "C" of the shaft 201 with the protective sheath 1600 and optical fiber 1300 inserted therein.

During a medical procedure, it is important to maintain the distance "X" that the optical fiber 1300 extends out of the tip 204 of the medical device 200 in order to ensure even lasing operation. Therefore, the optical fiber 1300 and its protective sheath 1600 should be secured in some fashion to the medical device 200 so as to prevent such movement of the optical fiber 1300. To this end, dual couplers 1610, 1620 are employed.

Each of the couplers 1610, 1620 is constructed so that it may securely hold a cable or other structure passing through its central bore. As an example, the couplers 1610, 1620 may be Tuohy-Borst fittings. The first coupler 1610 attaches to the interface 202 so that after passing the sheathed optical fiber 1300 through it, the coupler 1610 may be turned so as to compress an O-ring 1611 within it around the sheath 1600 and optical fiber 1300 to secure them in place. The sheath 1600 in this case is also compressible to an extent so that when the O-ring 1611 compresses it, it is forced against the optical fiber 1300 passing through it so as to hold the optical fiber 1300 in place.

However, because the O-ring 1611 is not being compressed directly against the optical fiber 1300, the optical fiber 1300 may slip in the sheath 1600 and disadvantageously move during the medical procedure. For this reason, a second coupler 1620 may be employed that is attached to a proximal end of the sheath 1600 so that after passing the optical fiber 1300 through it, the coupler 1620 may be turned so as to compress an O-ring 1621 within it around the optical fiber 1300 to secure the optical fiber 1300 in place.

The first coupler 1610 is attached to the interface 202, for example, by a luer-lock fitting (not shown), which is a tapered twist-lock connection. The coupler 1610 is thus free to slide along the sheath 1600 until secured to the sheathed fiber 1300 as described above. This allows the sheath 1600 to be positioned accurately in relation to the medical device 200 and facilitates different length medical devices and medical device tips. The second coupler 1620 is attached to the proximal end of the sheath 1600, for example, by a similar tapered, twist-lock connection. Alternatively, other well known attaching means may be used.

Although the various aspects of the present invention have been described with respect to one or more preferred embodiments, it will be understood that the invention is entitled to full protection within the full scope of the appended claims.

I claim:

1. A method for using a medical device in a medical system, the medical device having a wrist joint to orient a distal tip of the medical device, the method comprising:
   controllably actuating the wrist joint to manipulate a tip of the medical device so as to point towards a target tissue and activating a laser beam through an optical fiber extending through the medical device to a distal end of the tip so as to sever a portion of the target tissue; and
   controllably actuating the wrist joint to manipulate the tip of the medical device so as to point towards a non-severed portion of the target tissue and providing first and second biomaterials through separate lumens of a catheter extending through the medical device to the distal end of the tip so as to apply a mixture of the first and second biomaterials to the non-severed portion of the target tissue.

2. The method according to claim 1, further comprising:
   removing the optical fiber from a lumen of the medical device after performing the selective severing operation; and
   inserting the catheter into the lumen after removing the optical fiber and before applying the mixture of the first and second biomaterials to the non-severed portion of the target tissue.

3. The method according to claim 1, further comprising:
   inserting the optical fiber through a first lumen of the medical device before performing the selective severing operation; and
   inserting the catheter through a second lumen of the medical device before applying the mixture of the first and second biomaterials to the non-severed portion of the target tissue.

4. The method according to claim 1, wherein selectively actuating the plurality of wrist joints comprises:
   manipulating an input device which is coupled to the wrist joint for selectively actuating the wrist joint.

5. The method according to claim 1, wherein the medical device is coupled to a robotic arm having a plurality of robotic arm joints, the method further comprising:
   controllably actuating the plurality of robotic arm joints to move the medical device so the tip of the medical device is disposed proximate to the target tissue before activating the laser beam through the optical fiber to sever the portion of the target tissue.

6. The method according to claim 5, wherein the controllably actuating the plurality of robotic arm joints comprises:
   manipulating an input device which is coupled to the plurality of robotic arm joints for controllably actuating the plurality of robotic arm joints.

7. The method according to claim 1, wherein the medical device is coupled to a robotic arm having a plurality of joints, the method further comprising:
   controllably actuating the plurality of robotic arm joints to move the medical device so the tip of the medical device is disposed proximate to the target tissue before applying the mixture of the first and second biomaterials to the non-severed portion of the target tissue.

8. The method according to claim 7, wherein the controllably actuating the plurality of robotic arm joints comprises:
   manipulating an input device which is coupled to the plurality of robotic arm joints for controllably actuating the plurality of robotic arm joints.

9. The method according to claim 1,
   wherein activating the laser beam through the optical fiber to sever the portion of the target tissue comprises: activating the laser beam through the optical fiber to sever the portion of the target tissue so as to cut a hole in the target tissue; and
   wherein providing the first and second biomaterials through the separate lumens of the catheter extending through the medical device to the distal end of the tip so as to apply the mixture of the first and second biomaterials to the non-severed portion of the target tissue comprises: providing the first and second biomaterials through the separate lumens of the catheter extending through the medical device to the distal end of the tip so as to apply the mixture of the first and second biomaterials to the non-severed portion of the target tissue so as to seal the hole in the target tissue.

10. The method according to claim 1,
    wherein activating the laser beam through the optical fiber to sever the portion of the target tissue comprises: activating the laser beam through the optical fiber to sever the portion of the target tissue so as to sever tissue from adjoining tissue of the target tissue; and
    wherein providing the first and second biomaterials through the separate lumens of the catheter extending through the medical device to the distal end of the tip so as to apply the mixture of the first and second biomaterials to the non-severed portion of the target tissue comprises: providing the first and second biomaterials through the separate lumens of the catheter extending through the medical device to the distal end of the tip so as to apply the mixture of the first and second biomaterials to the non-severed portion of the target tissue and adhere the non-severed adjoining tissue of the target tissue together.

* * * * *